US00PP20482P2

(12) United States Plant Patent
Hanes

(10) Patent No.: US PP20,482 P2
(45) Date of Patent: Nov. 17, 2009

(54) ***PELARGONIUM* PLANT NAMED 'CANTE FIR09'**

(50) Latin Name: ***Pelargonium* sp.**
Varietal Denomination: Cante Fir09

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/218,559

(22) Filed: Jul. 16, 2008

(51) Int. Cl.
*A01H 5/00* (2006.01)

(52) U.S. Cl. ..... Plt./324

(58) Field of Classification Search ..... Plt./324, Plt./332, 325
See application file for complete search history.

*Primary Examiner*—June Hwu
(74) *Attorney, Agent, or Firm*—S. Matthews Edwards

(57) ABSTRACT

A new *Pelargonium* plant named 'Cante Fir09,' particularly distinguished by the bold fire-red flower color, semi-trailing habit of ivy types, heat tolerance of zonal types, foliage that has good resistance to edema, dense plant habit and excellent branching.

1 Drawing Sheet

Latin name of the genus and species of the plant claimed: *Pelargonium* sp.

Varietal denomination: 'Cante Fir09'.

BACKGROUND OF THE NEW PLANT

The present invention comprises a new *Pelargonium* botanically known as *Pelargonium interspecific*, hereinafter referred to by the variety name 'Cante Fir09.'

'Cante Fir09' is a product of a planned breeding program. The new cultivar 'Cante Fir09' has a bold fire-red flower color, semi-trailing habit of ivy types, heat tolerance of zonal types, foliage that has good resistance to edema, dense plant habit and excellent branching.

'Cante Fir09' originated from a hybridization in a controlled breeding program in Gilroy, Calif. USA. The female parent was an unpatented hybrid seedling identified as '9618-1' with dark red color. '9618-1' has less vigor, smaller plant habit and is a *Pelargonium hortorum* hybrid compared to 'Cante Fir09.'

The male parent of 'Cante Fir09' was an unpatented hybrid seedling identified as '9906-7' with red color. '9906-7' has less vigor, lighter foliage, a more irregular plant shape and is a *Interspecific* hybrid compared to 'Cante Fir09.'

'Cante Fir09' was selected as one flowering plant within the progeny of the stated cross in 2005 in a controlled environment in Gilroy, Calif. USA.

The first act of asexual reproduction of 'Cante Fir09' was accomplished when vegetative cuttings were propagated from the initial selection in the January 2005 in a controlled environment in Gilroy, Calif. USA.

Horticultural examination of plants grown from cuttings of the plant initiated in August 2005 in Gilroy, Calif. USA, and continuing thereafter, has demonstrated that the combination of characteristics as herein disclosed for 'Cante Fir09' are firmly fixed and are retained through successive generations of asexual reproduction.

'Cante Fir09' has not been observed under all possible environmental conditions. The phenotype may vary significantly with variations in environment such as temperature, light intensity and day length.

Plant Breeder's Rights for this cultivar were applied for in Canada on Aug. 23, 2007 and in Germany on Jul. 2, 2007. 'Cante Fir09' has not been made publicly available more than one year prior to the filing of this application.

BRIEF DESCRIPTION OF THE NEW VARIETY

The accompanying photographic drawing shows typical flower and foliage characteristics of 'Cante Fir09' with colors being as true as possible with an illustration of this type. The photographic drawing shows a flowering potted plant of the new variety and a close-up of the flowers.

DETAILED BOTANICAL DESCRIPTION

The measurements were taken in Gilroy, Calif. USA, in August 2007 on plants that were growing in 14 inch containers, containing three plants each. Culture of these plants started in the greenhouse in April 2007 and were transferred to the outdoor containers in early June 2007. The plants were approximately 4–5 months old.

Color Chart used: Royal Horticultural Society Colour Chart (R.H.S.) 2001.

BRIEF SUMMARY OF INVENTION

The following observations, measurements, and comparisons describe plants grown outside in Gilroy, Calif., USA. The following traits have been repeatedly observed and are determined to be basic characteristics of the new variety. The combination of these characteristics distinguishes this *Pelargonium* as a new and distinct variety.

TABLE 1

DIFFERENCES BETWEEN THE NEW VARIETY AND A SIMILAR VARIETY

| | 'Cante Fir09' | 'Cante Dered' (U.S. Plant Pat. No. 15,616) |
|---|---|---|
| Foliage | Darker | Lighter |
| Flowers | Larger and more floriferous | Smaller and less floriferous |

TABLE 1-continued

| DIFFERENCES BETWEEN THE NEW VARIETY AND A SIMILAR VARIETY | | |
|---|---|---|
| | 'Cante Fir09' | 'Cante Dered' (U.S. Plant Pat. No. 15,616) |
| Pedicels | Longer with anthocyanins | Shorter with no anthocyanins |

Plant:

*Form, growth and habit.*—Upright, outwardly spreading and mounded plant habit.

*Plant height.*—16–18 cm.

*Plant height* (*inflorescence included*).—20–25 cm.

*Plant width.*—20–25 cm.

Foliage:

*Arrangement.*—Alternate, simple.

*Immature, leaf color, upper surface.*—RHS 137A. Lower surface: Between RHS 137B and RHS137C.

*Mature, leaf color, upper surface.*—RHS 137A. Lower surface: Between RHS 137B and RHS137C.

*Length.*—4.5–4.7 cm.

*Width.*—7.3–7.7 cm.

*Shape.*—Orbicular.

*Base shape.*—Auriculate.

*Apex shape.*—Rounded.

*Margin.*—Lobed, almost angulate-like and broadly crenate.

*Texture, upper surface.*—Hirsute, heavily at the margins.

*Texture, lower surface.*—Hirsute, heavily on veins.

*Color of zone.*—No zone.

*Color of veins, upper surface.*—RHS 144A.

*Color of veins, lower surface.*—RHS 144A.

*Petioles color.*—RHS 144A.

*Petioles length.*—6–9 cm.

*Diameter of petiole.*—0.2–0.3 cm.

*Texture.*—Hirsute.

Stem:

*Color of stem.*—RHS 144A; anthocyanins in irregular patches of RHS 183D.

*Length of stem.*—10–16 cm.

*Diameter.*—0.6–0.7 cm.

*Length of internodes.*—1.5–2.0 cm.

*Texture.*—Hirsute.

Inflorescence:

*Type.*—An umbel composed of 20–30 flowers and buds.

*Umbel diameter.*—10–12 cm.

*Umbel depth.*—6–7 cm.

*Color of peduncle.*—Closest to RHS 187A, but a little more greyed.

*Length of peduncle.*—10–17.5 cm.

*Peduncle diameter.*—0.3–0.4 cm.

*Texture.*—Hirsute; glandular hairs.

*Pedicel color.*—RHS 187A.

*Length of pedicel.*—3.5–5.0 cm.

*Diameter of pedical.*—0.3 cm.

*Texture.*—Hirsute; glandular hairs.

Corolla:

*Form.*—Polypetalous, single with little overlapping to upper and lower petals.

*Number of petals.*—5.

*Width of flower.*—4.5–5.0 cm.

*Flower depth.*—1.5–2.0 cm.

*Color upper petals, upper surface.*—RHS 46B but more red; fades to RHS 53B; Light RHS N187A veins becoming RHS 186B basally.

*Color upper petals, lower surface.*—RHS 53B.

*Length of upper petals.*—2.4–2.5 cm.

*Width of upper petals.*—1.3–1.4 cm.

*Color lower petals, upper surface.*—RHS 46B but more red; fades to RHS 53B.

*Color lower petals, lower surface.*—RHS 53B.

*Length of lower petals.*—2.0–2.1 cm.

*Width of lower petals.*—2.2–2.4 cm.

*Petal shape.*—Obovate.

*Apex shape.*—Rounded.

*Margin.*—Entire.

*Petal texture.*—Papillose, both surfaces.

*Number of petaloids.*—None.

*Duration of flowering.*—Continuous flowering throughout the Summer.

*Lastingness of flowers.*—About one week.

Bud (when sepals first divide):

*Color.*—RHS 46B, but more velvety red.

*Length.*—0.6–0.7 cm.

*Width.*—1.3–1.6 cm.

*Shape.*—Broadly lanceoate to elliptical.

*Number of sepals.*—5, fused at the base.

*Color of sepals.*—Closest to RHS 178A, with a RHS 144A apex.

*Length of sepals.*—1.1–1.2 cm.

*Width of sepals.*—0.35–0.5 cm.

*Sepal shape.*—Broadly lanceolate.

*Apex shape.*—Acute.

*Margins.*—Entire.

*Texture,upper surface.*—Smooth.

*Lower surface.*—Hirsute; glandular hairs.

Reproductive organs:

*Pistil.*—1.

*Length.*—0.9–1.0 cm.

*Style color.*—RHS 58A.

*Style length.*—0.2 cm.

*Stigma color.*—RHS 58A.

*Number of anthers.*—8.

*Length filaments.*—0.6–0.7 cm.

*Color of filaments.*—RHS N155B but whiter with RHS 67A at the anther.

*Pollen amount.*—Moderate.

*Color of pollen.*—RHS N25A.

*Fertility/seed set.*—Not observed on this hybrid.

Disease/pest resistance: Disease resistance and/or susceptibility has not been observed on this hybrid.

What is claimed is:

1. A new and distinct variety of *Pelargonium* plant named 'Cante Fir09,' substantially as illustrated and described herein.

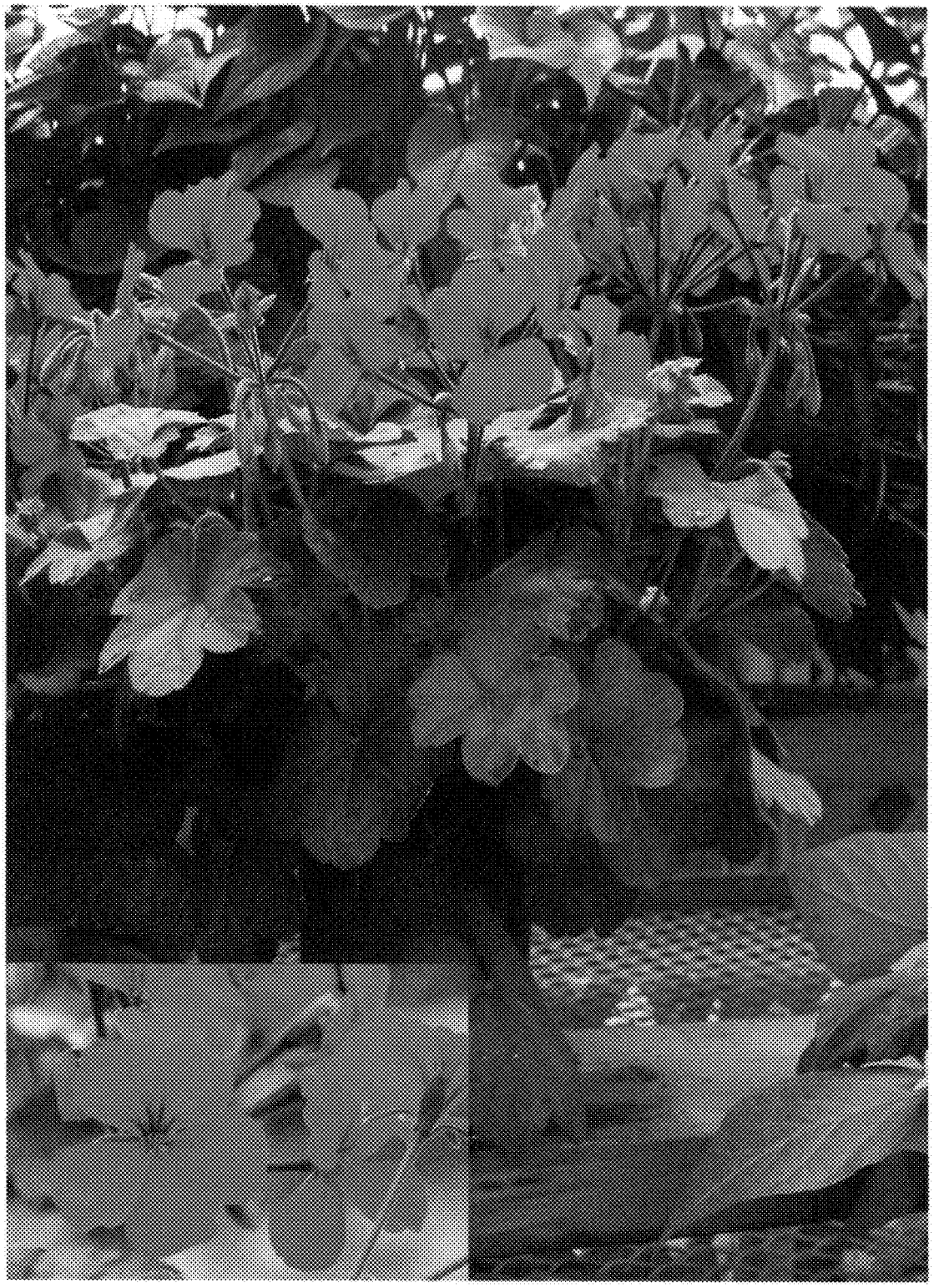

* * * * *